United States Patent
Soundarrajan et al.

(10) Patent No.: US 9,459,235 B2
(45) Date of Patent: Oct. 4, 2016

(54) INTERFERENCE COMPENSATED PHOTOIONIZATION DETECTOR

(71) Applicant: RAE Systems, Inc., San Jose, CA (US)

(72) Inventors: Prabhu Soundarrajan, Dublin, CA (US); Peter C. Hsi, Dublin, CA (US)

(73) Assignee: Honeywell International Inc., Morris Plains, NJ (US)

( * ) Notice: Subject to any disclaimer, the term of this patent is extended or adjusted under 35 U.S.C. 154(b) by 324 days.

(21) Appl. No.: 14/046,801

(22) Filed: Oct. 4, 2013

(65) Prior Publication Data

US 2014/0097853 A1 Apr. 10, 2014

Related U.S. Application Data

(60) Provisional application No. 61/709,930, filed on Oct. 4, 2012.

(51) Int. Cl.
*G01N 27/62* (2006.01)
*G01N 27/66* (2006.01)

(52) U.S. Cl.
CPC ..................... *G01N 27/66* (2013.01)

(58) Field of Classification Search
CPC ....................................... G01N 27/66
USPC ......................................... 324/464
See application file for complete search history.

(56) References Cited

U.S. PATENT DOCUMENTS

| | | |
|---|---|---|
| 4,778,998 A | 10/1988 | Carnahan |
| 5,393,979 A | 2/1995 | Hsi |
| 5,561,344 A | 10/1996 | Hsi |
| 5,773,833 A | 6/1998 | Hsi |
| 6,225,633 B1 | 5/2001 | Sun et al. |
| 6,313,638 B1 | 11/2001 | Sun et al. |
| 6,320,388 B1 | 11/2001 | Sun et al. |
| 6,333,632 B1 | 12/2001 | Yang et al. |
| 6,509,562 B1 | 1/2003 | Yang et al. |
| 6,661,233 B2 | 12/2003 | Yang et al. |
| 6,734,435 B2 | 5/2004 | Sun et al. |
| 6,967,485 B1 | 11/2005 | Hsueh et al. |
| 2004/0005715 A1* | 1/2004 | Schabron ............ G01N 27/626 436/104 |
| 2011/0137568 A1 | 6/2011 | Bradley et al. |
| 2011/0281367 A1 | 11/2011 | Walte et al. |
| 2012/0143515 A1 | 6/2012 | Norman et al. |

OTHER PUBLICATIONS

U.S. EPA, Chapter VI, Methods for the Analysis of Petroleum Hydrocarbons (1997), pp. VI-1 to VI-52.
Haag, Werner et al., RAE Systems Inc., The PID Handbook Theory and Applications of Direct-Reading Photoionization Detectors (PIDs)(ISBN:0-9768162-1-0),(2011) pp. i-198.
Europe Patent Application No. 13843563, Extended European Search Report, dated May 19, 2016, 7 pages.

* cited by examiner

*Primary Examiner* — Daniel Miller
(74) *Attorney, Agent, or Firm* — Conley Rose, P.C.; Kristin Jordan Harkins

(57) ABSTRACT

An integrated sensor of volatile organic gas can include a photoionization detector (PID) and one or more additional detectors such as an infrared detector, a catalytic combustion detector, or an electrochemical detector. One embodiment includes a methane detector that allows correction of the PID measurements for the interference of methane with the PID and/or allows a combination of measurements of the sensors to measure a total hydrocarbon concentration. A further sensor of non-hydrocarbon quenching gases such as carbon dioxide may also be used in correction of the PID measurements.

20 Claims, 3 Drawing Sheets

INTERFERENCE COMPENSATED PHOTOIONIZATION DETECTOR

CROSS-REFERENCE TO RELATED APPLICATIONS

This patent document claims benefit of the earlier filing date of U.S. provisional patent application No. 61/709,930, filed Oct. 4, 2012, which is hereby incorporated by reference in its entirety.

BACKGROUND

Refineries, chemical plants, and other manufacturing facilities often need or are required by law to monitor emissions. Airborne or vapor emissions may be monitored, for example, to avoid or detect atmospheric concentrations of chemicals that might create: unhealthy or illegal emissions to the environment outside the facilities; unhealthy or illegal chemical exposures of personnel; or risks of fire or explosions. In particular, industrial facilities that handle petroleum commonly employ detectors that measure Total Organic Vapor (TOV) or Total Petroleum Hydrocarbon (TPH) to ensure compliance with environmental regulations and for personnel and asset safety. Several types of chemical detectors are currently in use to measure TOV or TPH.

Flame ionization detectors (FIDs) are common for measurement of TOV or TPH. FIDs typically use a hydrogen flame to ionize organic vapors in the air or sample gas passing by the flame, and an electrical measurement of the resulting ions can then indicate the concentration of organic vapors exposed to the flame. FIDs can detect and measure a broad range of hydrocarbons from the lightest, i.e., methane or $C_1$, up to the heaviest hydrocarbons that may be of interest, e.g., $C_{11}$. FIDs are thus good detectors of TOV and TPH, but FIDs also have drawbacks. In particular, FIDs are generally more sensitive to aliphatic (or chained) hydrocarbons because aliphatic hydrocarbons burn more efficiently than do aromatic (or ringed) hydrocarbons. Also, FIDs may be inconvenient to use because FIDs require a supply of hydrogen, e.g., a hydrogen generator or regularly refilled or replaced hydrogen canisters. The flame in a FID may also create risks.

Photoionization detectors (PIDs) use an ultraviolet lamp to ionize organic vapors so that ionized organic compounds can be electrically measured. PIDs do not require a hydrogen supply or a flame and can be simply operated using portable or readily available electrical power. PID may also be more accurate than FIDs and some other types of detectors and may provide measurements with accuracies in the parts-per-million (ppm) range. However, PIDs may be most sensitive to aromatic hydrocarbons (e.g., BTEX compounds, benzene, toluene, ethylbenzene, and xylenes), which have lower ionization energies than to some lighter aliphatic hydrocarbons, but PIDs can also efficiently detect heavier aliphatic hydrocarbons, particularly if the PIDs employ UV lamps producing photons with shorter wavelength and therefore higher photon energies. PIDs are thus excellent at detecting heavier hydrocarbons that present the greatest health risks. However, light aliphatic hydrocarbons such as methane ($CH_4$), ethane ($C_2H_6$), or propane ($C_3H_8$), which are sometimes referred to herein as $C_1$, $C_2$, or $C_3$, have ionization energies that are higher than the photon energies of UV lamps commonly employed in PIDs, making many PIDs inefficient at detecting lighter hydrocarbons. As a result, current PIDs may not provide accurate TOV or TPH measurements. Also, PID measurements of volatile organic compounds (VOCs) are known to be sensitive to moisture and methane because water and methane molecules can partially absorb the UV light from the UV lamp and cause a VOC reading to drop when there is a high level of moisture or methane in the gas samples. (See, for example, U.S. Pat. No. 4,778,998.)

Current infrared (IR) detectors are effectively spectrophotometers that can measure hydrocarbon concentrations by measuring absorption of IR radiation at specific wavelengths, typically wavelengths between about 3.3 and 3.5 microns, characteristic of the hydrogen-carbon bonds of petroleum hydrocarbons. IR detectors can be used to measure hydrocarbons but may not uniformly detect all hydrocarbons. In particular, lighter hydrocarbons may have absorption peaks in the range of an IR detector, but the peaks in the absorption spectra of some heavier hydrocarbons may lie at the edge of or outside the detection range of an IR detector.

Some other systems for measuring organic vapors that have been considered include pellistors, catalytic hydrocarbon detectors, detector tubes, fiber optic chemical sensors, colorimetric test kits, turbidimetric test kits, and immunoassay test kits.

BRIEF DESCRIPTION OF THE DRAWINGS

The drawings illustrate examples for the purpose of explanation and are not of the invention itself. Use of the same reference symbols in different figures indicates similar or identical items.

DETAILED DESCRIPTION

In accordance with an aspect of the current invention, a detector system can employ a photoionization detector (PID), one or more additional detectors that use other measurement techniques to measure one or more chemical species not measured by the PID, and logic for combining measurements from the detectors. For example, an additional detector can measure the concentration of methane or a non-hydrocarbon chemical species that may interfere with operation of the PID and/or measure the concentration of hydrocarbons that may not be efficiently detected using just the PID. In one particular implementation, a detector system including a PID and a hydrocarbon detector can measure the concentration of total hydrocarbons and in the process correct for the quenching or other interference effects of methane or other interferents on PID measurements. More generally, detector logic may correct each PID measurement for detected interferents and/or may combine the corrected measurement from the PID with measurements from one or more of the additional hydrocarbon detectors to provide a total hydrocarbon measurement, e.g., a Total Organic Vapor (TOV) or Total Petroleum Hydrocarbon (TPH) measurement.

In another implementation, the detector system includes a PID and an infrared detector. The infrared detector may include a Non Dispersive InfraRed (NDIR) sensor tuned to specifically detect methane ($CH_4$) or to detect a group of light aliphatic hydrocarbons such as methane ($CH_4$), ethane ($C_2H_6$), propane ($C_3H_8$), butane ($C_4H_{10}$) and pentane ($C_5H_{12}$), sometimes referred to herein as $C_2$ to $C_5$ or light hydrocarbons. Additionally or alternatively, an interferent detector may detect non-hydrocarbon interferents such as water ($H_2O$) or carbon dioxide ($CO_2$) that may interfere with PID measurements but are not themselves organic vapors. Logic in the detector system can correct PID measurements based on measurements of one or more interferents such as methane and carbon dioxide measured by the additional detectors and can combine measurements from the same or different additional detectors to produce a TOV or TPH measurement.

Figure 1:
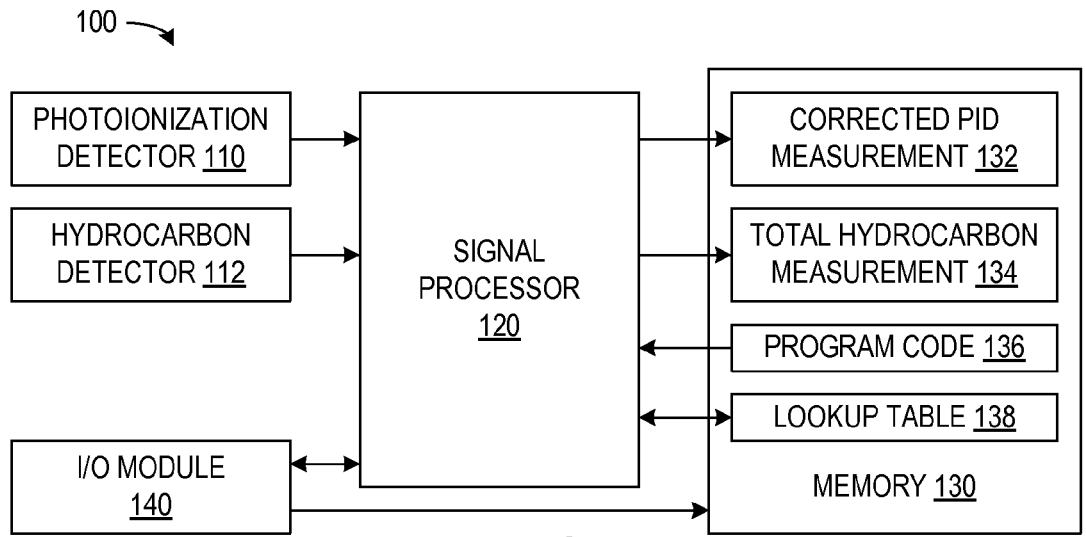
FIG. 1 shows one implementation of an integrated sensor combining a photoionization detector and an additional hydrocarbon detector.

FIG. 1 shows one specific example of an integrated detector system 100 capable of measuring a broad class of chemicals or total hydrocarbons, e.g., capable of TOV or TPH measurements. In particular, detector 100 may measure most or all expected organic vapors including but not limited to: light hydrocarbons, e.g., methane ($C_1$), ethane ($C_2$), propane ($C_3$), butane ($C_4$), and pentane ($C_5$); aromatic hydrocarbons, e.g., benzene, toluene, ethylbenzene, and xylenes; and longer chain hydrocarbons $C_6$ to $C_{26}$. As a result, detector system 100 may replace and perform the functions of an FID.

Integrated detector 100 combines a photoionization detector 110 with an additional hydrocarbon detector 112 and a signal processor 120 that processes and combines the measurement indicators from detectors 110 and 112. Photoionization detector 110 may use conventional photoionization sensing techniques in which photons from a UV lamp in detector 110 ionize organic vapors in a gas sample and an electronic circuit measures an ion current to infer the concentration of ionizable organic vapors in the gas sample. In general, photoionization detector 110 may inefficiently sense (or be unable to sense) light aliphatic hydrocarbons such as methane. Further, the methane may interfere with the operation of PID 110 by absorbing or quenching UV photons that could otherwise ionize measured organic vapors. Hydrocarbon detector 112 could employ any sensing technology or process capable of detecting a suitable range of concentrations of hydrocarbons including methane. For example, hydrocarbon detector 112 may be a metal oxide sensor, InfraRed (IR) sensor, a pellistor or catalytic combustion sensor capable, or an electrochemical detector of measuring a range of methane and/or light hydrocarbon concentration from about 500 ppm to 100%. In general, hydrocarbon detector 112 may be able to measure high concentrations of light hydrocarbons that PID 110 does not measure, but hydrocarbon detector 112 does not require the sensitivity or high accuracy that PID 110 may achieve for measurement of aromatic hydrocarbons or longer chain hydrocarbons.

Signal processor 120 uses measurement signals from both detectors 110 and 112 to calculate or otherwise determine a corrected PID measurement 132 or a total hydrocarbon measurement 134, e.g., a total VOC or TPH measurement. (In general, total hydrocarbon measurement 134 may not be intended to include all hydrocarbons but may include just a subset or class of hydrocarbons.) In one implementation, signal processor 120 is a microcontroller that receives measurement signals from photoionization detector 110 and hydrocarbon detector 112 and executes a program that may be stored as program code 136 in accessible memory 130 of signal processor 120. More generally, signal processor 120 can be any circuit capable of generating a representation of corrected PID measurement 132 or total hydrocarbon measurement 134 from the measurement signals detectors 110 and 112 provide.

In the illustrated configuration, signal processor 120 can correct the photoionization measurements using an indicator of methane concentration from hydrocarbon detector 112. In particular, methane is known to absorb UV photons that have insufficient photon energy to ionize a methane molecule. The absorption reduces the effective UV intensity, i.e., the number of UV photons, available to ionize the organic vapors that photoionization detects. As a result, the presence of methane in a gas sample that photoionization detector 110 measures may reduce the measurement signal from photoionization detector 110. Signal processor 120 may use the measurement from detector 112 to determine a correction to apply to the raw measurement from photoionization detector 110 in order to provide a corrected PID measurement 132 that more accurately indicates the concentration of VOCs that photoionization detector 110 measures. FIG. 1 illustrates an example where signal processor 120 can use the measurement from detector 112 as an index to a lookup table 138 containing correction factors, and in determining corrected PID measurement 132, signal processor 120 may scale the photoionization measurement signal (e.g., an indicator of a measured ion current) from photoionization detector 110 up by the correction factor processor 120 identified in lookup table 138 using the measurement indicator from hydrocarbon detector 112. More generally, signal processor 120 can employ a formula or other technique to determine corrected PID measurement 132 from the outputs of detectors 110 and 112. Further, signal processor 120 can provide total hydrocarbon measurement 134 by adding or otherwise combining corrected measurement 132 and a measurement that detector 112 provides.

Sensor system 100 in the illustrated implementation further includes an input/output module 140, which may provide a user interface for local operation of sensor system 100 and a communication interface. For example, I/O module may include an RFID sensor, a bar code scanner, and a WiFi or other wireless module. A bar code reader or an RFID sensor may be used to read the code on a valve or other element in the pipeline or facility to identify elements or locations associated with a measurement. The wireless module may enable communications with a remote system or control center that can evaluate and correlate measurements from multiple mobile or fixed sensors that may be located throughout a facility.

System 100 may be integrated as a unit that can be portable, battery operated or be used in a fixed location and powered with an AC/DC power source, a battery, or solar packs. In general, since system 100 can provide a total hydrocarbon measurement 134, system 100 can be used in any application that currently employs an FID. However, system 100 does not require a supply of hydrogen or other quickly depleted consumables as some other broadband sensors such as FIDs require, and system 100 does not require a flame.

Figure 2:
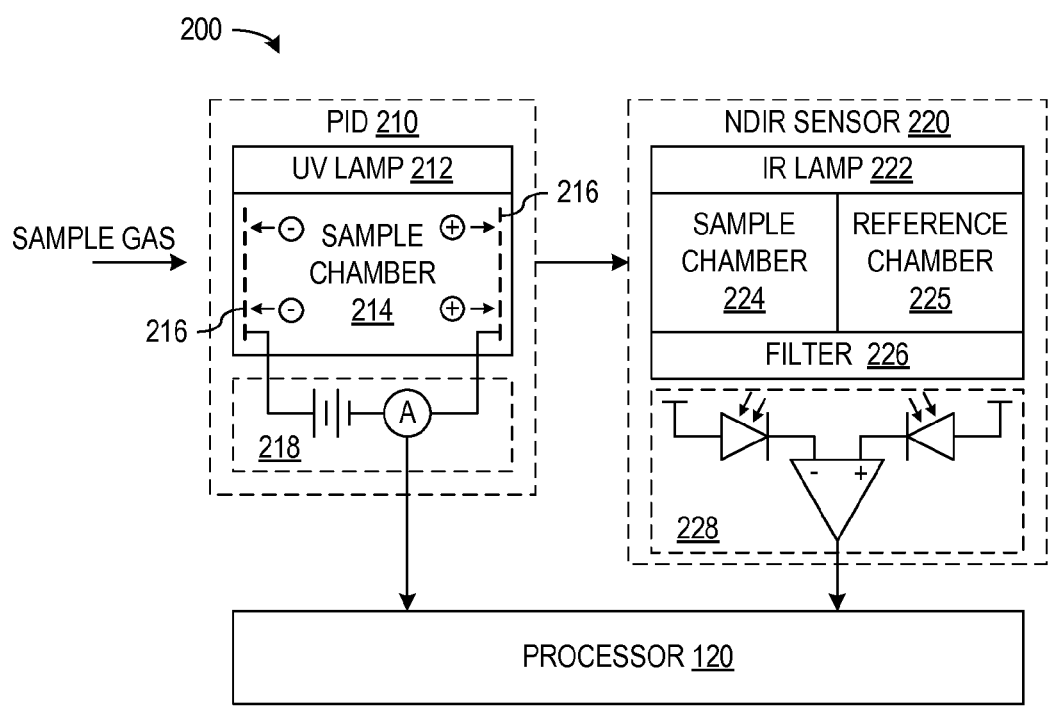
FIG. 2 shows one implementation of an integrated sensor combining a photoionization detector and an infrared-based hydrocarbon detector.

FIG. 2 shows a specific implementation of a sensor system 200 employing a PID 210, an NDIR sensor 220, and a processor circuit 120 that combines measurements from PID 210 and NDIR 220. In the illustrated configuration, PID 210 includes a UV lamp 212 positioned to direct ionizing photons, e.g., photons with energies between about 9.8 eV and 11.7 eV, into a sample chamber. Sample chamber 214 contains a gas having a composition to be measured. In general, the sample gas is air from an environment being tested and may be introduced to sample chamber 214 through an inlet, a dust filter, a moisture filter, or other mechanisms (not shown) for permitting the flow of gas. An active system such as a fan or pump (not shown) can also be used to create or control the flow of air or other gas sample through sample chamber 214. Ionizing photons from UV lamp 212 can efficiently ionize molecules, e.g., organic vapor, having ionization energies lower than the photon energy to thereby create positive ions and free electrons. The ions and electrons are attracted to respective positively and negatively biased electrodes 216, which creates an electrical current that an electrical circuit 218 measures. Given a fixed UV lamp performance, e.g., an intensity and a photon energy distribution that are effectively constant, the current that circuit 218 measures may be substantially proportional to the concentration of ionizable molecules in the sample gas. More generally, the measured current is functionally related to the constituents of the sample gas. Processor 120 receives a measurement signal indicating the magnitude of the ion current and can use the functional relationship to determine a measurement of ionizable molecules in the sample gas.

NDIR sensor 220 employs an infrared (IR) lamp 222 to illuminate a sample chamber 224 and a reference chamber 225 with light that includes infrared light. Sample chamber 224 receives the sample gas, e.g., air from the environment being tested and since PID 210 and NDIR sensor 220 are non-destructive of the volatile compounds measured, sample chamber 224 may be serially positioned before or after sample chamber 214 along a fluid or air flow path to and from the surrounding environment. Reference chamber 225 may be a sealed chamber containing a known concentration, e.g., a zero concentration, of the type of molecule or molecules that NDIR sensor 220 detects. For example, reference chamber 225 may contain air with no measurable concentration of volatile organic compounds. The light from IR lamp 222 includes one or more frequency components having an energy corresponding to a peak in the absorption spectrum of each molecular species to be detected. For example, methane has an absorption spectrum that efficiently absorbs light having a wavelength between about 2.9 and 3.1 µm or between about 1.3 and 1.4 µm. Ethane has an absorption spectrum with a peak for light with a wavelength of about 2.9 µm. Accordingly, the target component of illumination from IR lamp 222 having a wavelength characteristic of a peak in the absorption spectra of the target molecule or molecules to be detected will be depleted by absorption in sample chamber 224 if the target molecule or molecules are present, but if the sealed reference chamber 225 is free of molecules that absorb the target component, the intensity of that wavelength component will not be reduced when traversing reference chamber 225. A measurement circuit 228 can thus measure a difference between the intensity of the target wavelength component passing through reference chamber 225 and the intensity of the target wavelength component passing through sample chamber 224, and the measured difference indicates the concentration of the target molecules in sample chamber 224.

In the implementation of FIG. 2, an optical filter 226 selectively transmits light in a wavelength band including the target wavelength or wavelengths, so that broadband light detectors such as conventional photodiodes can selectively detect the target wavelength or wavelengths of light. In some implementations, filter 226 may have multiple sections or operating modes that selectively transmit different infrared wavelength bands, so that NDIR 220 can provide separate measurements of different chemical species. For example, one implementation of filter 226 may include a first section or mode that selectively transmits a band corresponding to an absorption peak for methane, a second section or mode that selectively transmits a band corresponding to absorption peaks of light hydrocarbons $C_2$ to $C_5$, and a third section or mode that selectively transmits a band corresponding to an absorption peak for carbon dioxide. NDIR 220 could thus provide separate indicators of the respective concentrations of different chemical species in the gas sample.

Processor 120 receives the measurement signals from PID 210 and NDIR sensor 220 and can combine the measurement signals to improve the accuracy of the measured concentration of organic vapors that photoionization detector 110 measures and/or to provide a total hydrocarbon measurement.

Figure 3:
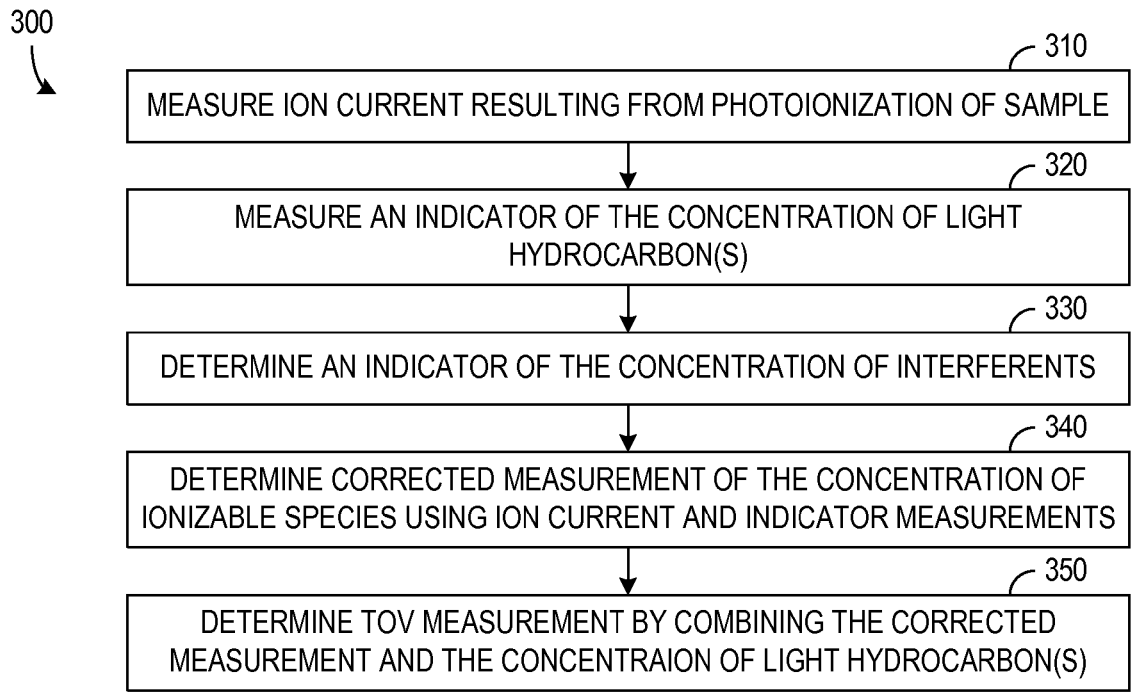
FIG. 3 is a flow diagram of a process for using a photoionization measurement with other measurements of organic vapors.

FIG. 3 is a flow diagram illustrating one implementation of a process 300 for using PID and light hydrocarbon and/or methane measurements to improve the accuracy of PID measurements and to provide total hydrocarbon measurements. Process 300 includes measurements or determinations 310, 320, and 330 respectively of a current of ions that photoionization creates in a gas sample and of an indicator of light hydrocarbons, methane, and/or interferents in the gas sample. As noted above, the measured ion current is related to the concentration of organic vapor that the PID can ionize. The indicator of the concentration of light hydrocarbons, methane, or interferents can be, for example, an NDIR detector measurement of the absorption of target IR wavelengths in the sample gas. In general, an indicator of the concentration of light hydrocarbons can include indicators of multiple separate measurements, e.g., an indicator of methane concentration and an indicator of the concentration of one or more other aliphatic hydrocarbons.

Figure 4:
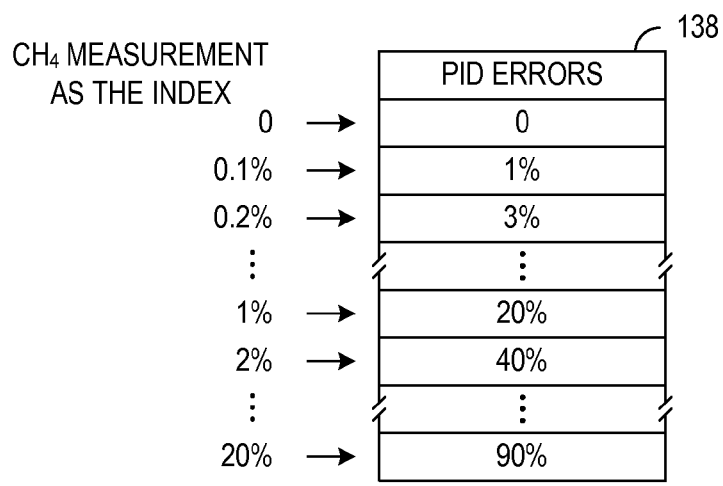
FIG. 4 shows a lookup table containing correction factors indexed by measured light hydrocarbon concentration.

Block 340 of process 300 determines a corrected measurement of the concentration of species that the PID can ionize. In particular, the ion current measured in the PID can be converted into a raw measurement of organic vapor concentration using conventional techniques such as multiplying the ion current by a conversion factor, using the ion current as an index to a lookup table containing concentration values, or using the ion current as the argument of a function that relates the ion current to concentration. However, the raw PID measurement thus determined may be in error due to interferents in the sample gas, and block 330 may correct the raw PID measurement. For example, FIG. 4 shows one implementation of lookup table 138 that may contain experimentally determined errors in the raw PID measurement corresponding to measured methane concentrations. In general, the contents or entries of such a lookup table will depend on the specific characteristics of the PID such as the energy of photons from the UV lamp and the geometry of the lamp, sample chamber, and electrodes in the specific PID. Step 340 can include using a lookup table, formula, or other mechanism to use a measurement or indicator of the interferent concentration to determine a correction to the raw PID measurement. In particular, if a methane concentration is separately determined in step 320 and carbon dioxide concentration is determined in step 330, the measured methane concentration may provide an index for identifying one correction factor in one lookup table, and the measured carbon dioxide concentration may provide an index for identifying another correction factor in another lookup table. For example, using lookup table 138 of FIG.

4, a measurement indicating a 0.2% concentration of methane identifies a PID error of 3%, and the raw PID measurement can be increased by 3% to compensate for the effects of methane. Similar corrections can be applied for any other measured interferents. A measurement of light hydrocarbons could similarly be used to determine the index.

Several molecular species are known to be interferents that have some effects, e.g., quenching, on PID measurements. However, critical interferents are molecular species that may occur at concentrations having a significant effect on the PID measurement and may significantly vary in concentration at different measurement locations. In general, some interferents do not normally appear at concentrations that significantly alter PID measurements or have relatively constant concentrations in all air samples. Some interferents such as water vapor, which have concentrations that vary significantly in air, may be filtered out of or otherwise removed from a sample being measured. However, methane may appear at high concentration, e.g., up to 20% or more in gas samples, and methane is an important contribution to TOV and TPH measurements. Accordingly, methane is a particularly important interferent to measure and use in PID measurement such as illustrated by process 300. However, concentrations of other interferents such as carbon dioxide can also be measured and used in block 340 when correcting the PID measurement.

Process 300 in block 350 can further use the corrected PID measurement and a measurement of light hydrocarbons to produce a total hydrocarbon measurement. The combination may be a simple addition of one or more of the light hydrocarbon measurement to the concentration of species that the PID measured. More generally, a PID and a light hydrocarbon detector may have an overlap in the chemical species measured, and the total hydrocarbon measurement may be a result of a linear or non-linear combination of PID and other hydrocarbon detector measurements.

Figure 5:
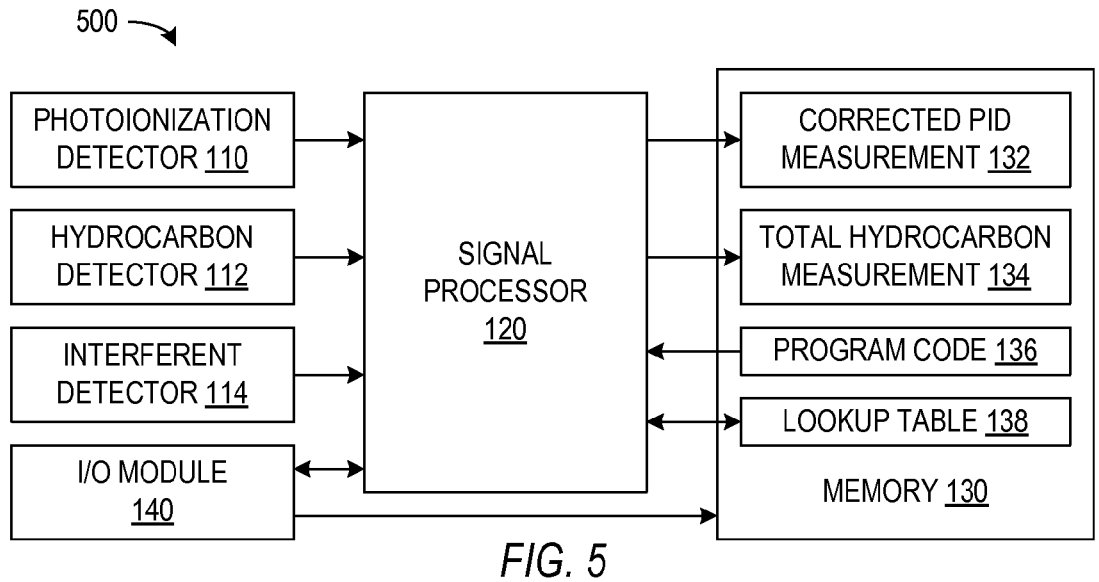
FIG. 5 shows one implementation of an integrated sensor combining a photoionization detector, an additional hydrocarbon detector, and an interferent detector.

FIG. 5 shows an implementation of a detector system 500 that uses a photoionization detector 110 with a methane/light hydrocarbon detector 112 as described above with reference to FIG. 1 but also employs an additional interferent detector 114. Interferent detector 114 may be tuned to detect non-hydrocarbon gas molecules. In detector system 500, the PID measurement can be corrected for both methane and the effects of non-hydrocarbon interference gases. Further, the determination of total hydrocarbons can combine the corrected PID measurement with a measurement of methane/light hydrocarbon from detector 112. The combination may provide an accurate PID measurement or an accurate total hydrocarbon measurement by measuring both hydrocarbon and non-hydrocarbon interferents and correcting for their interference effects in PID detector 110.

Figure 6:
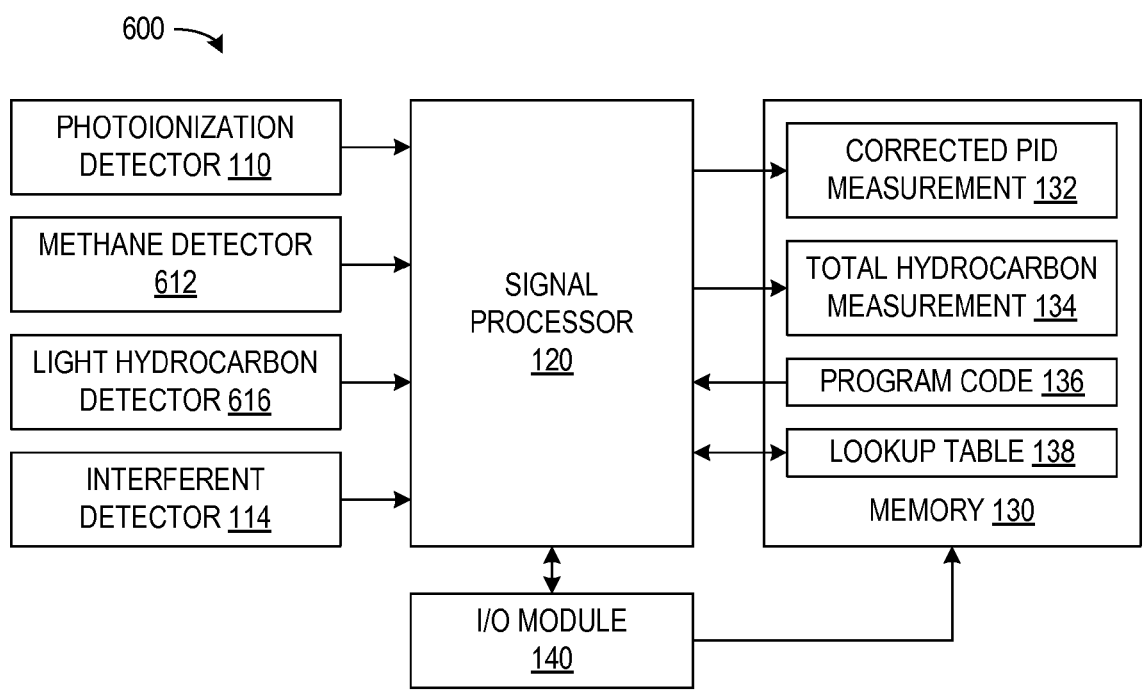
FIG. 6 shows one implementation of an integrated sensor combining a photoionization detector, a methane detector, a light hydrocarbon detector, and an interferent detector.

FIG. 6 shows an implementation of a detector system 600 that uses a photoionization detector 110 with a methane detector 612, a light hydrocarbon detector 616, and an interferent detector 114. As described above, interferent detector 114 may be tuned to detect non-hydrocarbon chemical species such as carbon dioxide. Methane detector 612 may particularly be tuned to detect a concentration of methane in a gas sample, and light hydrocarbon detector 616 may be tuned to detect a concentration of $C_2$ to $C_5$, i.e., ethane, propane, butane, and pentane with or without including methane in the measured concentration. Each of detectors 114, 612, or 616 may be an infrared detector that measures light absorption in an infrared wavelength band chosen for the gas or gases (e.g., methane, carbon dioxide, or $C_2$ to $C_5$) that the detector detects. In detector system 600, the PID measurement can be corrected for both methane and the effects of non-hydrocarbon interference gases. Further, the determination of a total hydrocarbon concentration can combine the corrected PID measurement with a measurement of light hydrocarbons from detector 616 and if necessary, a measurement of methane concentration from detector 612. The combination may provide an accurate total hydrocarbon measurement by measuring and compensating for both hydrocarbon and non-hydrocarbon interferents of the PID measurement and covering a full range of hydrocarbon species using a combination of PID detector 110 with additional detectors 612 and 616.

As described above, embodiments of detector systems can combine one or more sensor technologies to overcome the interference and measurement limitations associated with PID technology and to measure compounds that PIDs don't accurately detect. Some applications for such detectors include but are not limited to: measuring BTEX (benzene, toluene, ethylbenzene, and xylenes) affluent from oil-water separator systems; Emergency Response, HAZMAT; Wing Tank Entry Petroleum Products; Fugitive emissions leak detection; Landfill Monitoring; Natural Gas Pipeline Leak Detection; and Shale Gas safety.

Although particular implementations have been disclosed, these implementations are only examples and should not be taken as limitations. Various adaptations and combinations of features of the implementations disclosed are within the scope of the following claims.

What is claimed is:

1. A gas detector system comprising:
a photoionization detector;
one or more additional detectors to detect one or more chemical species that the photoionization detector does not detect; and
a processing circuit coupled to the photoionization detector and the one or more additional detectors, wherein the processing circuit is configured to:
determine an indication of a concentration of at least one chemical species of the one or more chemical species that the photoionization detector does not detect using the one or more additional detectors;
determine a correction factor to apply to an output of the photoionization detector based on the indication of the concentration of the at least one chemical species of the one or more chemical species;
apply the correction factor to the output of the photoionization detector; and
produce a corrected output of the photoionization detector in response to the application of the correction factor.

2. The system of claim 1, wherein the one or more additional detectors comprise an infrared detector, a catalytic combustion detector, or an electrochemical detector.

3. The system of claim 1, wherein the one or more additional detectors comprises a hydrocarbon detector, and wherein the one or more chemical species comprises one or more hydrocarbons that the photoionization detector does not detect.

4. The system of claim 3, wherein the processing circuit is further configured to combine an output of the hydrocarbon detector with the corrected output of the photoionization detector to produce a total hydrocarbon concentration measurement.

5. The system of claim 3, wherein the hydrocarbon detector detects a methane concentration.

6. The system of claim 1, wherein the one or more additional detectors comprise:
a methane detector; and
a detector of light hydrocarbons.

7. The system of claim 6, wherein the one or more additional detectors further comprise an interferent detector configured to detect a non-hydrocarbon chemical species that causes interference effects on the photoionization detector.

8. The system of claim 7, wherein the non-hydrocarbon chemical species is carbon dioxide.

9. The system of claim 7, wherein the processing circuit is configured to use an output from the methane detector and an output from the interferent detector in determining a correction factor for an output from the photoionization detector.

10. The system of claim 9, wherein the processing circuit further combines the output from the methane detector and an output from the detector of the light hydrocarbons with the corrected output of the photoionization detector to produce a total hydrocarbon concentration measurement.

11. The system of claim 1, wherein the one or more additional detectors comprise an interferent detector configured to detect a non-hydrocarbon chemical species that causes interference effects on the photoionization detector.

12. The system of claim 11, wherein the non-hydrocarbon chemical species is carbon dioxide.

13. The system of claim 1, further comprising a lookup table containing the correction factors and having an index depending on the indication of the concentration from the one or more additional detectors.

14. A method comprising:
measuring an ion current generated in a gas sample in a photoionization detector;
measuring the gas sample to determine a first indicator of a first concentration of one or more chemical species that the photoionization detector does not detect;
determining a correction factor to apply to the ion current generated in the gas sample in the photoionization detector based on the first indicator of the first concentration of the one or more chemical species that the photoionization detector does not detect;
applying the correction factor to the ion current generated in the gas sample in the photoionization detector; and
producing a second indicator of a second concentration of chemical species ionized in the photoionization detector based on applying the correction factor to the ion current to correct for interference effects in the photoionization detector.

15. The method of claim 14, further comprising determining a measurement of total hydrocarbon concentration using a combination including the first indicator and the second indicator.

16. The method of claim 14, wherein measuring the gas sample to determine the first indicator comprises measuring a concentration of methane in the gas sample.

17. The method of claim 16, wherein measuring the gas sample to determine the first indicator further comprises measuring a concentration of a non-hydrocarbon chemical species in the gas sample.

18. The method of claim 15, further comprising measuring the gas sample to determine a third indicator of a concentration of light hydrocarbons, wherein the combination comprises the first indicator, the second indicator, and the third indicator.

19. A gas detector system comprising:
a photoionization detector configured to detect one or more chemical species;
one or more additional detectors to detect one or more additional chemical species while the photoionization detector detects the one or more chemical species, wherein the photoionization detector is not configured to detect the one or more additional chemical species; and
a processing circuit coupled to the photoionization detector and the one or more additional detectors, wherein the processing circuit is configured to:
apply a correction to a first output from the photoionization detector, wherein the correction is determined based on a second output from the one or more additional detectors that is indicative of a concentration of at least one chemical species of the one or more additional chemical species, and
produce a corrected output of the photoionization detector in response to the application of the correction to the first output.

20. The system of claim 19, wherein the one or more additional detectors comprise:
a methane detector; and
a detector of light hydrocarbons.

* * * * *